United States Patent [19]

Parker et al.

[11] Patent Number: 5,003,970
[45] Date of Patent: * Apr. 2, 1991

[54] ROLL FORM MEDICAL BANDAGING PRODUCT, METHOD OF CONSTRUCTING SAME AND CONTAINER FOR ROLL FORM BANDAGING PRODUCT

[75] Inventors: A. Bruce Parker, Charlotte; Donna F. Miller, Harrisburg, both of N.C.

[73] Assignee: Parker Medical Associates, Charlotte, N.C.

[ * ] Notice: The portion of the term of this patent subsequent to Sep. 13, 2005 has been disclaimed.

[21] Appl. No.: 477,021

[22] Filed: Feb. 8, 1990

Related U.S. Application Data

[60] Continuation-in-part of Ser. No. 243,585, Sep. 12, 1988, Pat. No. 4,899,738, which is a continuation of Ser. No. 243,584, Sep. 12, 1988, Pat. No. 4,869,046, which is a division of Ser. No. 815, Jan. 6, 1987, Pat. No. 4,770,299.

[51] Int. Cl.$^5$ ............... A61F 13/04; B65D 85/66
[52] U.S. Cl. ............... 128/90; 128/89 R; 128/156; 206/409; 206/389; 206/440
[58] Field of Search ............... 128/89 R, 90, 91 R, 128/156, 169; 206/389, 409, 411, 412, 413, 440, 447, 484, 484.2

[56] References Cited

U.S. PATENT DOCUMENTS

| 2,960,984 | 11/1960 | Parker | 128/91 R |
|---|---|---|---|
| 3,683,903 | 8/1972 | Fox et al. | 128/90 |
| 4,235,228 | 11/1980 | Gaylord, Jr. et al. | 128/91 R |
| 4,279,344 | 7/1981 | Holloway, Jr. | 206/631 |
| 4,411,262 | 10/1983 | von Bonin et al. | 128/90 |
| 4,442,833 | 4/1984 | Dahlen et al. | 128/90 |
| 4,454,874 | 6/1984 | Monnier | 128/91 R |
| 4,502,479 | 3/1985 | Garwood et al. | 128/90 |
| 4,570,622 | 2/1986 | von Bonin et al. | 128/90 |
| 4,628,917 | 12/1986 | Campagna, Jr. et al. | 128/90 |
| 4,770,299 | 1/1987 | Parker | 128/90 |
| 4,869,046 | 9/1989 | Parker | 53/416 |

FOREIGN PATENT DOCUMENTS

2055582 A  3/1981  United Kingdom .

Primary Examiner—Robert A. Hafer
Assistant Examiner—Kevin G. Rooney
Attorney, Agent, or Firm—W. Thad Adams, III

[57] ABSTRACT

An outer container (31) formed of moisture-impervious material having an elongate product dispensing sleeve (32) having a moisture-proof sealable opening (33) on one end and an enlarged product storage package (34) communicating with the dispensing sleeve (32). A medical material (14) is positioned within sleeve (32) and includes a substrate (16) formed of a suitable number of overlaid layers of a woven or knitted fabric such as fiberglass. Substrate (16) is contained within a tubular wrapping (18) formed of a soft, flexible non-woven fiber such as polypropylene. Substrate (16) is impregnated or coated with a reactive system which remains stable when maintained in substantially moisture-free conditions but which hardens upon exposure to sufficient moisture to form a rigid, self-supporting structure.

26 Claims, 6 Drawing Sheets

ROLL FORM MEDICAL BANDAGING PRODUCT, METHOD OF CONSTRUCTING SAME AND CONTAINER FOR ROLL FORM BANDAGING PRODUCT

This application is a continuation-in-part of Ser. No. 243,585 filed Sept. 12, 1988, Pat. No. 4,899,738, which is a continuation of Ser. No. 243,584 filed Sept. 12, 1988, Pat. No. 4,369,046, which is a divisional of Ser. No. 000,815 filed Jan. 6, 1987, Pat. No. 4,770,299.

TECHNICAL FIELD AND BACKGROUND OF THE INVENTION

The present invention relates generally to the field of orthopedic medicine and more specifically to the design of an improved medical bandage formed of a moisture-curable plastic material, a method for constructing such an improved medical bandage and a container for storing and dispensing such a roll form bandaging product.

Medical bandages for use in the treatment of injuries, such as broken bones requiring immobilization of a body member, are generally formed from a strip of fabric or scrim material impregnated with a substance which hardens into a rigid structure after the strip has been wrapped around the body member. The hardening substance traditionally used in carrying out this procedure is plaster-of-paris.

Conventional practice has been to fabricate a cast or splint upon an injured limb by initially applying to the limb a protective covering of a cotton fabric or the like and then overwrapping the covering and limb with a woven cloth impregnated with plaster-of-paris which has been wetted by dipping in water immediately prior to application. This practice is still in widespread use but possesses several significant disadvantages. For example, the above-described application procedure is messy and time consuming. Several components are required and considerable skill is necessary.

In order to alleviate the above-recited disadvantages of the conventional application procedure for plaster-of-paris casts and splints, unitary splinting materials have been devised and are disclosed in, for example, U.S. Pat. Nos. 3,900,024, 3,923,049, and 4,235,228. All of these patents describe a padding material with a plurality of layers of plaster-of-paris impregnated cloth. Such unitary splinting materials are not as messy and can be applied more quickly but still suffer from a number of disadvantages inherent in plaster-of-paris cast materials. All plaster-of-paris splints have a relatively low strength to weight ratio which results in a finished splint which is very heavy and bulky. Plaster-of-paris splints are slow to harden, requiring 24 to 72 hours to reach maximum strength. Since plaster-of-paris breaks down in water, bathing and showering are difficult. Even if wetting due to these causes can be avoided, perspiration over an extended period of time can break down the plaster-of-paris and create a significant problem with odor and itching.

A significant advance in the art of casting and splinting is disclosed in U.S. Pat. Nos. 4,411,262 and 4,502,479. The casting materials disclosed in these patents comprise a flexible fabric impregnated with a moisture-curing resin enclosed in a moisture-free, moisture-impervious package. Compared to plaster-of-paris, these products are extremely lightweight, have a very high strength to weight ratio and can be made relatively porous, permitting a flow of air through the casting material. Prior art moisture-curing systems include a package within which is contained a plurality of layers of fabric, such as fiberglass, impregnated with a moisture-curing resin. No provision is made for re-closing the package, so that the entire material must be very quickly used after removal from the package since such moisture-curing resins will cure in a relatively short period of time due merely to contact with atmospheric moisture.

From the above discussion, it can be seen that both the conventional plaster-of-paris casting method and the more recent moisture-curable resin casting method possess both advantages and disadvantages. On the one hand, plaster-of-paris casts are bulky, heavy and difficult to apply whereas moisture-curable resin casts are lightweight, durable and relatively easy to apply. Plaster-of-paris can be very easily stored and used as needed since it has a relatively long shelf life so long as it is not completely wetted. On the other hand, the moisture-curable resins are very sensitive to the presence of even minute amounts of moisture which requires that either the materials be packaged in a wide variety of different shapes and sizes or unused portions be discarded, generating a substantial amount of waste and increasing the effective cost of the product. This invention combines the advantages of both plaster-of-paris and moisture-curable resin systems while avoiding their respective disadvantages. This is accomplished by providing a unitary splinting system with improved strength and convenience. A unitary system is provided with the use of moisture-curing resin casting materials, together with a moisture-impervious package with means for resealing the package against entry of moisture after a desired length of bandaging product has been removed for use. In this manner, hardening of the bandaging product remaining in the moisture-impervious package is prevented thereby increasing the cost effectiveness of the system substantially.

SUMMARY OF THE INVENTION

It is therefore an object of the invention to provide a medical bandaging product in roll form with a moisture-curable resin which hardens the material upon exposure to moisture to form a rigid, self-supporting structure.

It is another object of the invention to provide a medical bandaging product which can be dispensed in any desired length while preventing hardening of the remaining material until use is desired.

It is another object of the invention to provide a unitary medical bandaging product which includes a wrapping to provide a cushion against the skin of a patient.

It is another object of the invention to provide a method of constructing a medical bandaging product having the characteristics and objects described above.

These and other objects and advantages of the present invention are achieved in the preferred embodiment disclosed below by providing a medical bandaging product in roll form for being dispensed in predetermined length suitable for a given medical use.

An outer container formed of moisture-impervious material encloses the bandaging product. The container comprises an elongate product dispensing sleeve having a moisture-proof sealable opening on one end and an enlarged product storage package communicating with the sleeve.

A medical material positioned in the container in substantially moisture-free conditions and sealed therein against entry of moisture until use. An elongate medical material is positioned within the sleeve and storage package and is sealed therein against entry of moisture until use.

The medical material comprises a substrate impregnated or coated with a reactive system which remains stable when maintained in substantially moisture-free conditions but hardens upon exposure to sufficient moisture to form a rigid, self-supporting structure. A soft, flexible protective wrapping encloses the substrate along its length to provide a cushioning barrier between the substrate and the skin of a patient when the material is in use.

A sealing device such as a moisture-impervious tape is provided for resealing the sleeve against entry of moisture after a predetermined length of the bandaging product has been dispensed for use to prevent hardening of the substrate remaining in the sleeve until use is desired. Other devices for resealing the sleeve comprise at least one resealable zipper formed in and adjacent one end of the sleeve, or a clamp for clamping closed the end of the sleeve.

The substrate preferably comprises a plurality of knitted or woven fabric layers of a material such as fiberglass.

The protective wrapping which encloses the substrate preferably comprises a non-woven cushion formed of polypropylene or some other hydrophobic fiber in the form of a tube within which the substrate is placed.

Preferably, the medical bandaging product is rolled into a coil and positioned in a dispenser carton having a slot through which the product is dispensed as needed.

In accordance with the method according to the present invention, a moisture-impervious product container comprising an elongate product dispensing sleeve sealable to prevent entry of moisture and a product storage package communicating with the sleeve is provided. An elongate medical material is positioned in the product storage package of the product container with one end of the material extendable into the dispensing sleeve for being dispensed in an appropriate desired length. One end of the medical material is positioned in a single layer which coextends with the sleeve in substantially moisture-free conditions and sealing the medical material in the sleeve and the product storage package against entry of moisture until use.

A container according to the invention is intended for an elongate medical bandaging product of the type characterized by having a substrate, a reactive system impregnated into or coated onto the substrate, the system remaining stable when maintained in substantially moisture-free conditions and hardening upon exposure to sufficient moisture to form a rigid, self supporting structure and a soft, flexible protective wrapping enclosing the substrate along its length to provide a cushioning barrier between the substrate and the skin of a patient when the material is in use. The container includes a moisture-proof product storage package for holding a predetermined long length of the medical bandage product in a compact form suitable for dispensing.

An elongate product dispensing sleeve communicates with the product storage package for receiving an end of the bandaging product therethrough. The sleeve has an open end through which the bandaging product is dispensed in predetermined lengths.

A seal is provided for resealing the open end of the sleeve against moisture penetration when the bandage product is not being dispensed.

BRIEF DESCRIPTION OF THE DRAWINGS

Some of the objects of the invention have been set forth above. Other objects and advantages of the invention will appear as the description of the invention proceeds when taken in conjunction with the following drawings, in which.

DESCRIPTION OF THE PREFERRED EMBODIMENT

Figure 1:
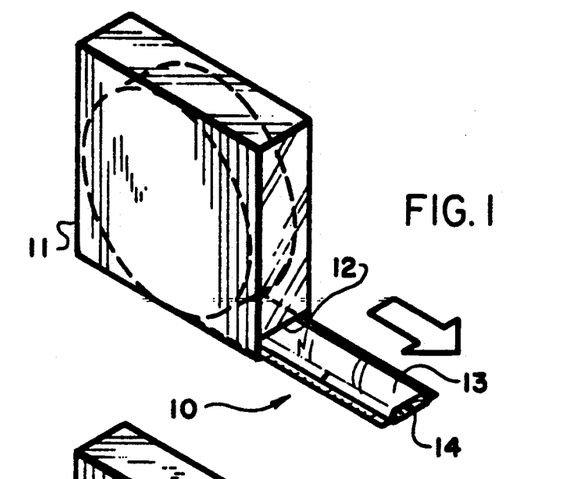
FIG. 1 is a perspective, schematic view showing the medical bandaging product being dispensed from a dispenser.

Referring now specifically to the drawings, a medical bandaging product according to the present invention is shown generally in FIG. 1 at 10. Bandaging product 10 may be sold in any convenient length, such as 24 feet, and is rolled into a coil and positioned in a suitable dispenser 11. Dispenser carton 11 is provided with a slot 12 at one lower corner through which bandaging product 10 extends.

Bandaging product 10 is comprised generally of an outer elongate sleeve 13 which is formed of a moisture-impervious material. Sleeve 13 is heat sealed along opposite, parallel extending sides to form an elongate tube. An elongate medical material 14, described in detail below, is positioned within sleeve 13 and is maintained in substantially moisture-free conditions until dispensed.

Figure 2:
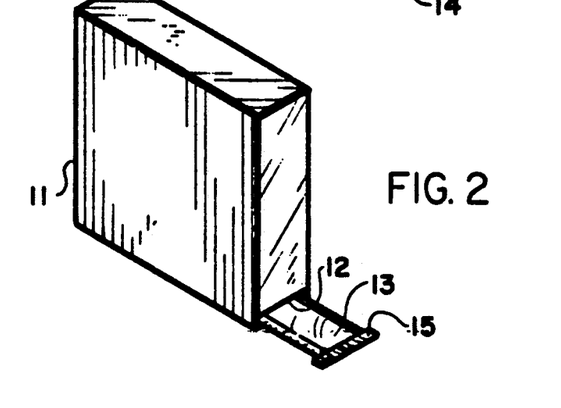
FIG. 2 is a view similar to FIG. 1, showing the unused portion of the medical bandaging product being resealed to prevent entry of moisture.

As is shown in FIG. 2, the end of sleeve 13 is sealed with sealing means, such as a moisture-impervious tape 15.

Other types of sealing mechanisms are possible such as, for example, a soft, conformable gasketing device with spring loaded compression, leverage clamping or screw action of sufficient strength to prevent entry of moisture into sleeve 13. One particularly suitable device (not shown) is a pair of spring loaded rollers which, as compression takes place rolls slightly backwards, pushing medical material 14 back slightly into sleeve 13 to permit a better seal.

Another possible sealing means (not shown) is a device which pushes the medical material 14 back into the sleeve 13 a sufficient distance (approximately one inch), so that the open end of sleeve 13 may be heat sealed once again.

Figure 3:
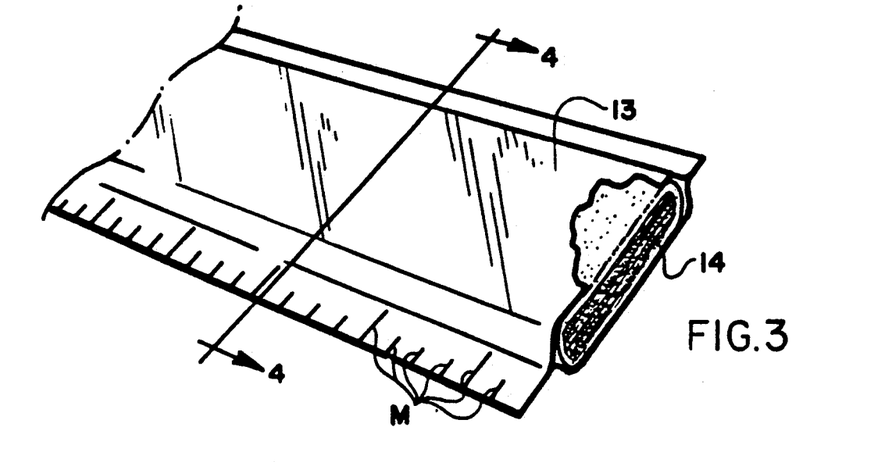
FIG. 3 is a perspective view with parts broken away of a cut length of medical material.

Since the appropriate length of medical material 14 is best determined by measurement, measurement marks "M" are printed on one edge of the sleeve 13, as is best shown in FIG. 3. Once the appropriate length of medical material 14 has been dispensed and cut from the roll, it is removed from sleeve 13 and sleeve 13 is discarded.

Figures 4, 5:
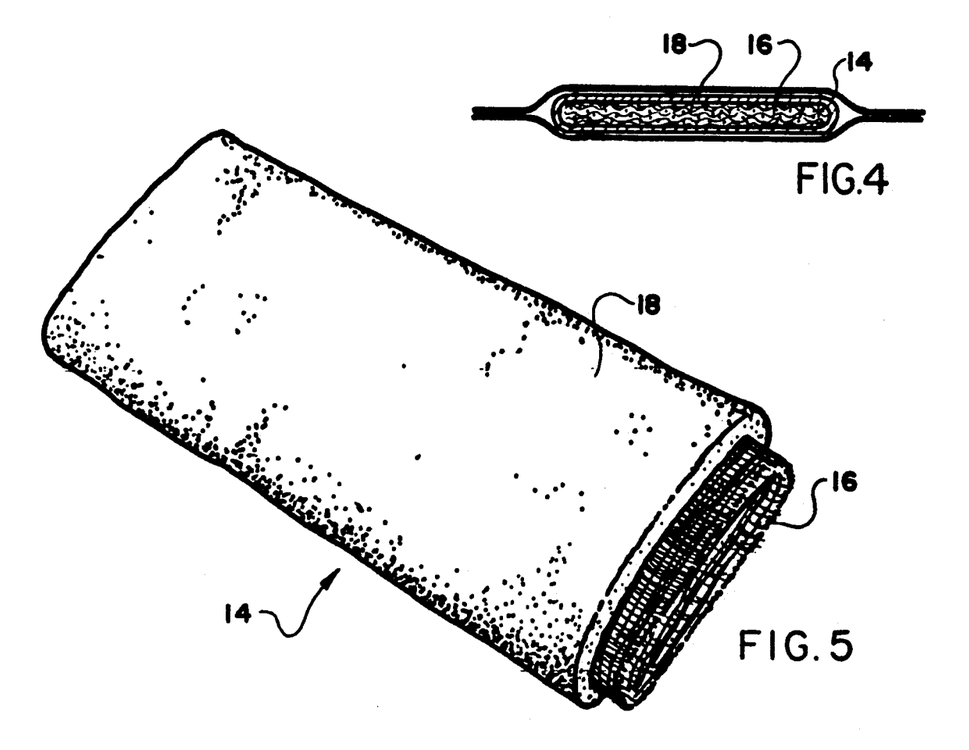
FIG. 4 is a vertical cross-section taken substantially along lines 4—4 of FIG. 3.
FIG. 5 is a perspective view of a length of the medical material with the substrate layer exposed for clarity.
Figure 6:
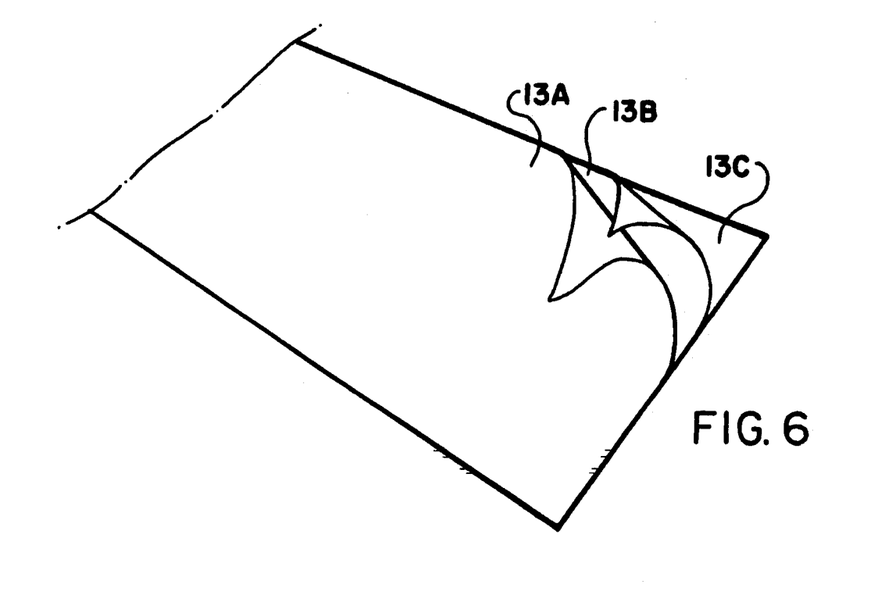
FIG. 6 is a perspective view illustrating the laminate structure of the elongate outer sleeve.

Referring now to FIGS. 4 and 5, medical material 14 comprises a substrate 16 comprised of a suitable number for example, 6, of overlaid layers of a woven or knitted relatively open fabric, such as fiberglass. Substrate 16 is contained within a tubular wrapping 18 which is formed of a soft, flexible non-woven fiber such as polypropylene or some other suitable hydrophobic fiber. This provides a cushioning protective layer between the skin of the patient and substrate 16. Substrate 16 is impregnated or coated with a reactive system which remains stable when maintained in substantially moisture-free conditions but which hardens upon exposure to sufficient moisture to form a rigid, selfsupporting structure. A typical formulation of the reaction system is set forth in the following table:

| Typical Formulation: | | | |
|---|---|---|---|
| Isonate ↓ 143L | or | | |
| Mondur ↓ CD | or | polyisocvanate | 50.0% |
| Rubinate ↓ XI168 | | | |
| Pluracol ↓ P1010 | | polyol | 46.6% |
| DC-200 Silicone | | defoaming agent | 0.30% |
| Benzoyl Chloride | | stabilizer | 0.10% |
| Thancat ↓ DM-70 | | catalyst | 3.0% |
| | | | 100% |

A complete discussion of the parameters of the reactive system, the manner of production and the variables which apply are found in U.S. Pat. No. 4,411,262, referred to above.

As in shown in FIG. 3, sleeve 13 is formed of two laminated elongate sheets placed in registration and heat sealed along its opposite sides to form a tube. The outer layer 13a is formed of a tear-resistant plastic film. The middle layer 13b comprises aluminum foil and acts as a moisture barrier. The inner layer 13c is a plastic film having thermoplastic properties suitable for heat sealing the interior of sleeve 13 securely against moisture.

Figure 7:
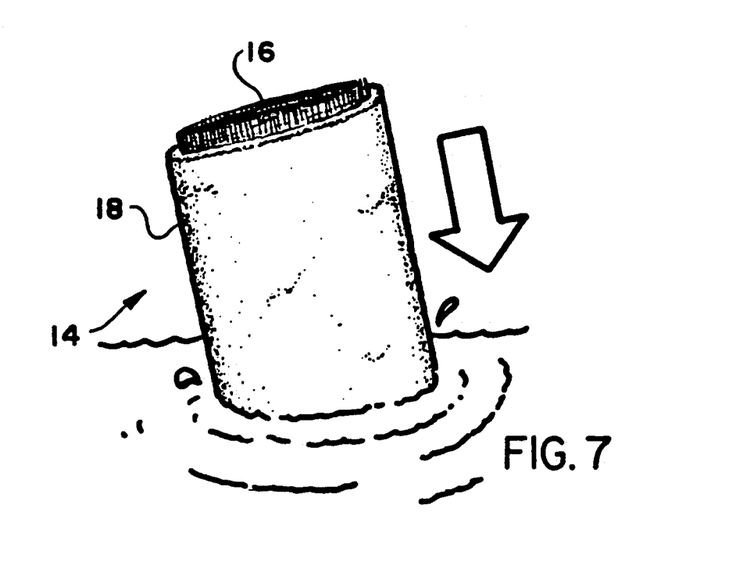
FIG. 7 illustrates activation of the moisture-curable resin of the invention by wetting.

As is shown in FIG. 7, moisture-curing is activated by dipping product 14 in water. Then excess moisture is squeezed from the structure.

Figure 8:
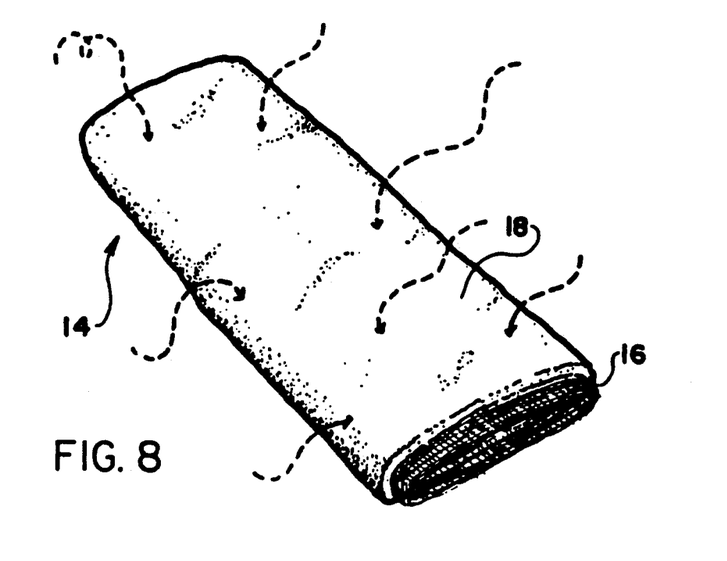
FIG. 8 illustrates activation of the reactive hardening system of the invention by contact with atmospheric moisture.

Alternatively, moisture-curing can take place over a longer period of time by allowing contact between the reactive system on substrate 16 and atmospheric moisture, as is illustrated in FIG. 8.

Figure 9:
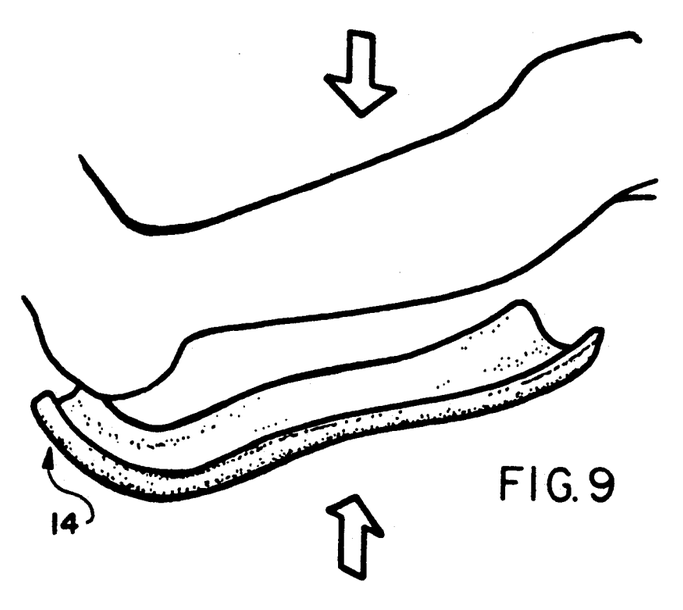
FIG. 9 shows the medical material after removal from the sleeve being formed to fit the contour of a body member.
Figure 10:
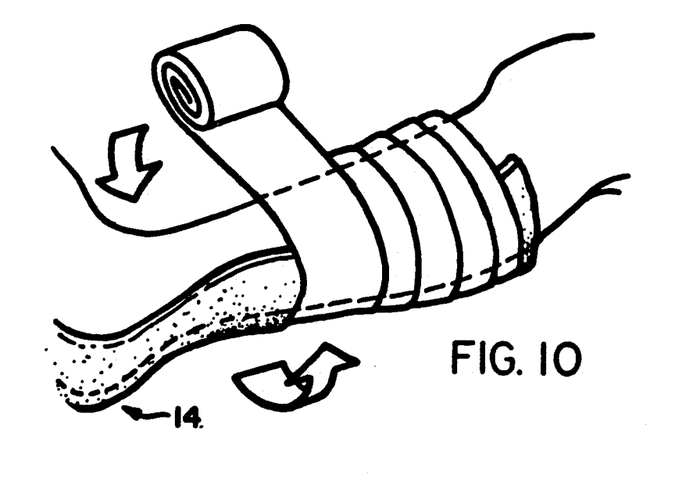
FIG. 10 is a perspective view of the hardening medical material being secured into place on a body member by means of a covering wrap.

Referring now to FIG. 9, an appropriate length of material 14 is formed to the shape of the body member to be immobilized. This particular type of splint, known as a posterior short leg splint, is formed by molding a length of the product 14 to the calf and up over the heel and onto the foot. Then, product 14 is overwrapped with an elastic conventional bandage, as is shown in FIG. 10.

Figures 11, 12:
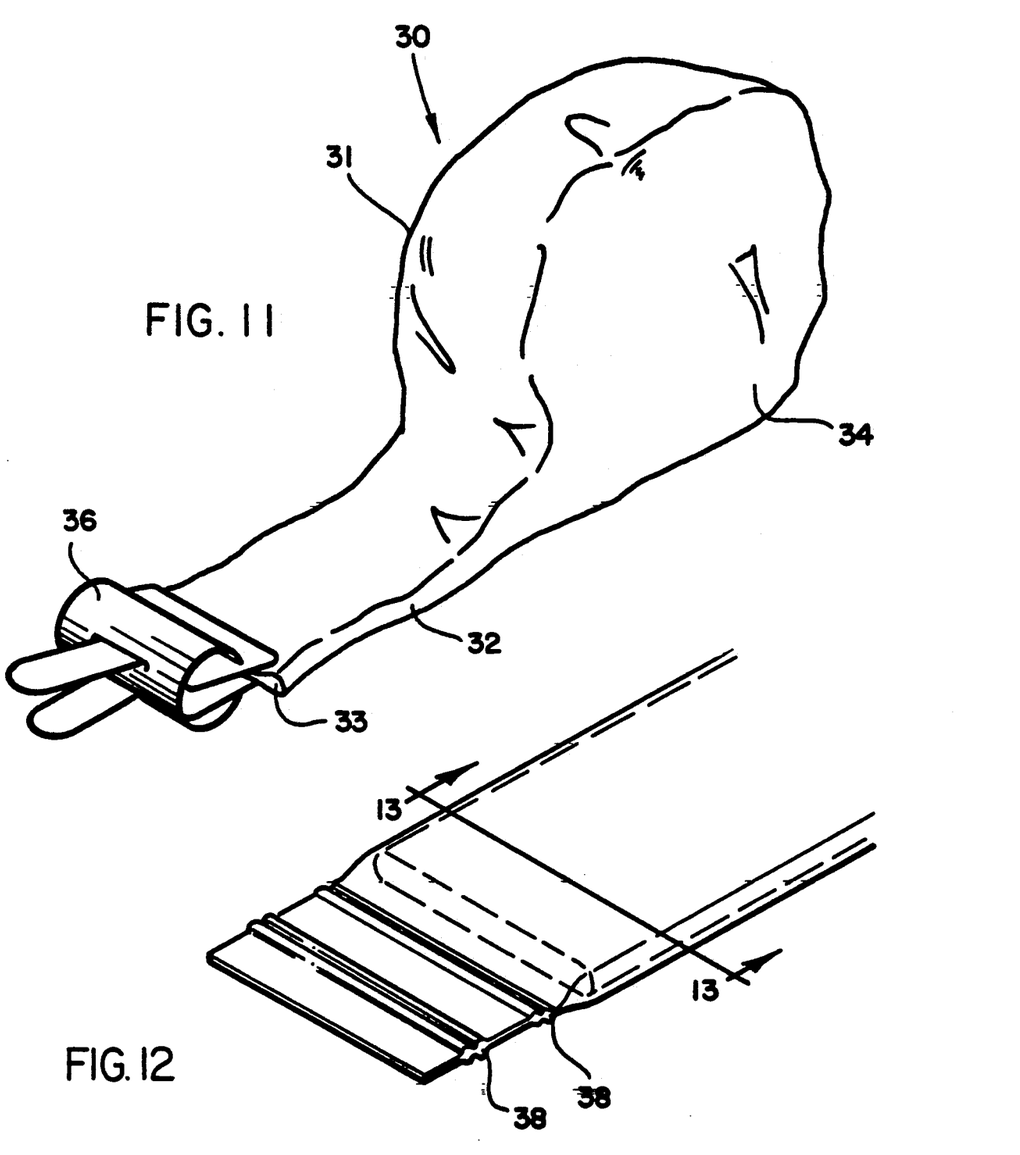
FIG. 11 is a perspective view of a dispensing container for holding the medical material.
FIG. 12 is a fragmentary perspective view of the openable end of the sleeve showing a double locking zipper integrally formed in the end for resealing the end of the sleeve after dispensing.

Referring now to FIG. 11, medical bandaging product according to another embodiment of the invention is shown at broad reference numeral 30. The medical material 14 is positioned within a container 31 which is formed of two laminated elongate sheets placed in registration and heat sealed along a common seam to form a moisture proof container of the same material and construction as the sleeve 13. The outer layer is formed of a tear-resistant plastic film and the middle layer comprises aluminum foil and acts as a moisture barrier. The inner layer is a plastic film having thermoplastic properties suitable for heat sealing the interior of container 31 securely against moisture.

As is also shown in FIG. 11, container 31 comprises an elongate dispensing sleeve 32 having an openable end 33 through which the medical material 14 in the container 31 is dispensed. A coil of the medical material 14 is positioned in an enlarged product storage package 34 which is integral and communicates with dispensing sleeve 32.

As is shown in FIGS. 11 and 12, the end 33 of dispensing sleeve 32 may be sealed with a clamp 36 of any suitable type, or a "zip-lock"-type integrally-formed zipper 38 of a type which is typical on sandwich bags and other food storage bags. As is shown in FIG. 12, a pair of spaced-apart zippers 38 insure against inadvertent release of one of the zippers 38 causing moisture to enter the container 31 and harden the medical material 14. Each zipper 38 comprises a groove defined by a pair of spaced-apart ridges on one surface of the dispensing sleeve 32 cooperating with a single ridge on the other surface of the dispensing sleeve 32 which is received by means by a press fit into the groove.

Figure 13:
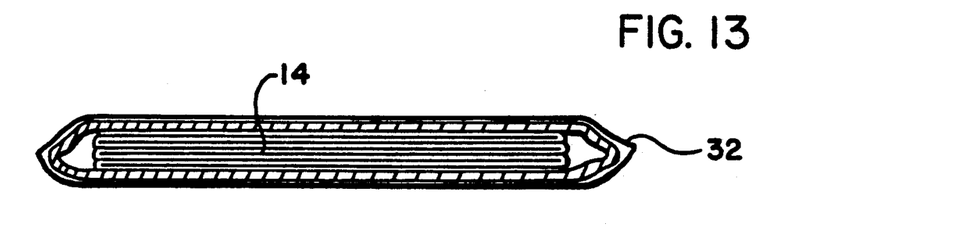
FIG. 13 is a view taken along lined 13—13 of FIG. 12.

As is shown in FIG. 13, dispensing sleeve 32 fits snugly around the medical material 14 in order to limit exposure of the medical material 14 to air which enters when the opening 33 is not sealed.

Figure 14:
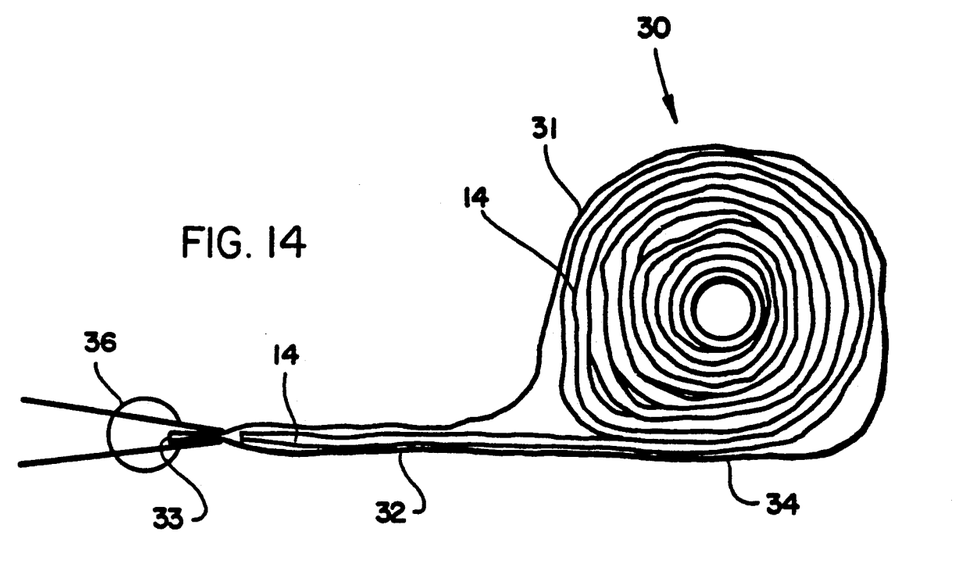
FIG. 14 is a vertical cross-section of the dispensing container shown in FIG. 11.

FIG. 14 shows that the medical material 14 is coiled into a relatively tight coil to limit exposure to air and sealed into the container 31. When opening 33 is properly sealed, container 31 is sufficiently airtight so that medical material 14 remains in its soft, uncured state for much longer that the usual length of time needed to exhaust the supply of medical material 14 in container 31. If a short length of the medical material 14 adjacent the opening 33 hardens, it can be cut away and discarded.

A desired length of medical material 14 is dispensed by removing clamp 36 or unzipping zippers 38 and grasping the exposed end of the medical material 14. The appropriate length is pulled out of container 31—the medical material 14 uncoiling in the storage package 34. When the proper length has been dispensed through opening 33, it is cut and the end is tucked back into the dispensing sleeve 32. The open end 33 is quickly resealed.

Figure 15:
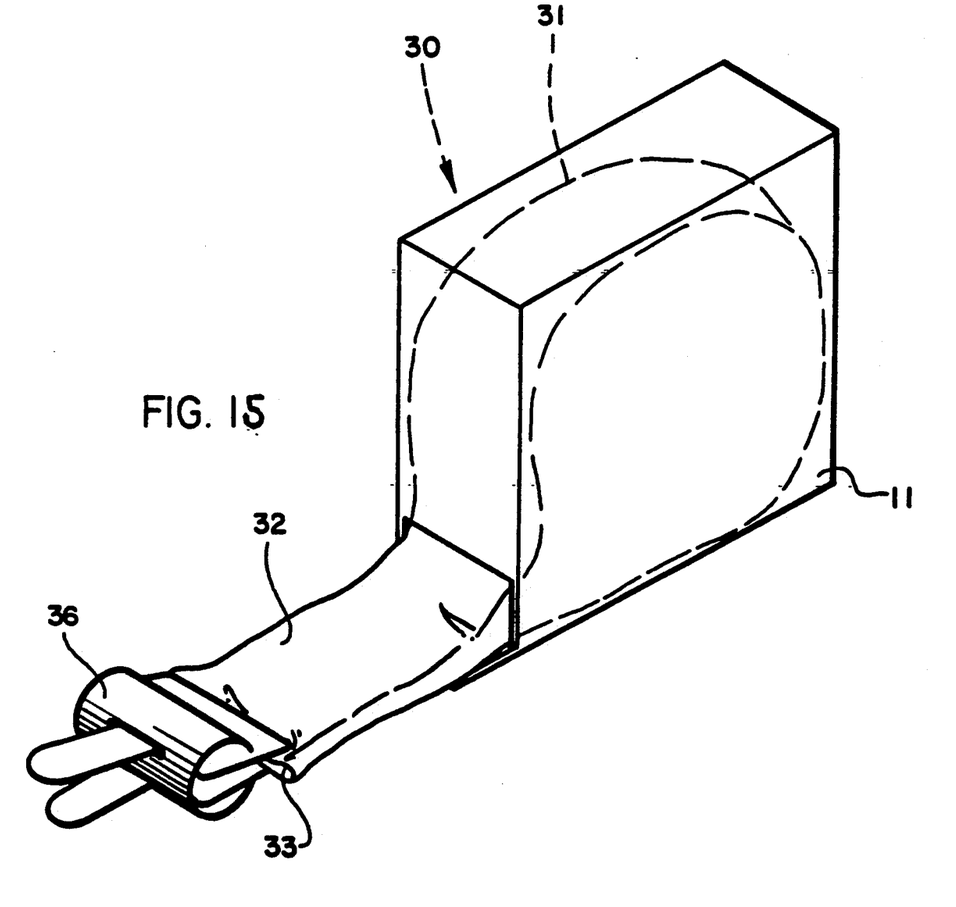
FIG. 15 is a perspective view of the dispenser carton into which the container is positioned.

If desired, the medical bandaging product 30 can be placed inside dispensing carton 11, with the dispensing sleeve 32 of container 31 projecting out of the slot in the bottom of carton 11.

A medical bandaging product and container is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A medical bandaging product for being dispensed in predetermined lengths suitable for a given medical use, comprising:
   (a) an outer container formed of moisture-impervious material, the container comprising an elongate product dispensing sleeve having a moisture-proof sealable opening on one end and an enlarged product storage package communicating with the dispensing sleeve;
   (b) a medical material positioned in the container in substantially moisture-free conditions and sealed therein against entry of moisture until use, the medical material comprising:
      (i) a substrate;
      (ii) a reactive system impregnated into or coated onto the substrate, the system remaining stable when maintained in substantially moisture-free conditions and hardening upon exposure to sufficient moisture to form a rigid, self supporting structure; and
      (iii) a soft, flexible protective wrapping enclosing the substrate along its length to provide a cushioning barrier between the substrate and the skin of a patient when the material is in use;
   (c) means for resealing the dispensing sleeve against entry of moisture after a predetermined length of the bandaging product has been dispensed for use to prevent hardening of the substrate remaining in the product container.

2. A medical bandaging product according to claim 1, wherein the container is fabricated of a aluminum foil laminate having an outer tear resistant layer, a central aluminum foil layer and an inner heat sealable plastic layer.

3. A medical bandaging product according to claim 1, wherein the substrate comprises a plurality of knitted or woven fabric layers.

4. A medical bandaging product according to claim 1, wherein the protective wrapping enclosing the substrate comprises a fibrous nonwoven cushion.

5. A medical bandaging product according to claim 4, wherein the protective wrapping enclosing the substrate comprises a nonwoven polypropylene tube.

6. A medical bandaging product according to claim 1, wherein the reactive system comprises a blended polyisocyanate, polyol, catalyst and stabilizer.

7. A medical bandaging product according to claim 1, wherein the means for resealing the dispensing sleeve comprises moistureimpervious tape.

8. A medical bandaging product according to claim 1, wherein the means for resealing the dispensing sleeve comprises at least one resealable zipper formed in and adjacent one end of the dispensing sleeve.

9. A medical bandaging product according to claim 1, wherein the means for resealing the dispensing sleeve comprises a clamp for clamping closed the end of the dispensing sleeve.

10. A medical bandaging product according to claim 1, wherein the medical material is in the form of a coil, and wherein the product storage package has a width substantially the same as the width of the medical material and has a peripheral shape which is substantially circular in cross-section and dimensioned to receive therein the coil of medical material.

11. A medical bandaging product according to claim 1, and including a dispenser carton within which the container is of medical material is contained.

12. A medical bandaging product according to claim 11, wherein the dispenser carton within which the product container is positioned includes a slot through which the leading end of the coil of medical material may be positioned and through which the medical material is dispensed as needed.

13. A medical bandaging product in roll form for being dispensed in predetermined lengths suitable for a given medical use, comprising:
   (a) an outer container formed of moisture-impervious material, the container comprising an elongate product dispensing sleeve having an moisture-proof sealable opening on one end and an enlarged product storage package communicating with the dispensing sleeve;
   (b) a medical material positioned in the container in substantially moisture-free conditions and sealed therein against entry of moisture until use, the medical material comprising:
      (i) a substrate formed of a plurality of knitted or woven fabric layers;
      (ii) a reactive system impregnated into or coated onto the substrate, the system remaining stable when maintained in substantially moisture-free conditions and hardening upon exposure to sufficient moisture to form a rigid, self supporting structure and comprising a blended polyisocyanate, polyol, catalyst and stabilizer; and
      (iii) a soft, flexible protective nonwoven tubular web enclosing the substrate along its length to provide a cushioning barrier between the substrate and the skin of a patient when the material is in use;
   (c) means for resealing the dispensing sleeve against entry of moisture after a predetermined length of the bandaging product has been dispensed for use to prevent hardening of the substrate remaining in the dispensing sleeve.

14. A medical bandaging product, comprising:
   (a) an outer container formed of moisture-impervious material, the container comprising an elongate product dispensing sleeve having an moisture-proof sealable opening on one end and an enlarged product storage package communicating with the dispensing sleeve;
   (b) a medical material positioned in the container in substantially moisture-free conditions and sealed therein against entry of moisture until use, the medical material comprising:
      (i) a substrate having first and second opposing sides defining therebetween a predetermined thickness;
      (ii) a reactive system impregnated into or coated onto the substrate, the system remaining stable when maintained in substantially moisture-free conditions and hardening upon exposure to sufficient moisture to form a rigid, self supporting structure; and
      (iii) a soft, flexible, protective, freely water and air permeable padding overlying both the first and second sides of the substrate contiguous thereto to provide a cushioning barrier between the substrate and the skin of a patient when the material is in use.

15. A medical bandaging product, consisting essentially of:
   (a) an outer container formed of moisture-impervious material, the container comprising an elongate dispensing sleeve having an moisture-proof sealable opening on one end and an enlarged product storage package communicating with the dispensing sleeve;
   (b) a medical material positioned in the container in substantially moisture-free conditions and sealed therein against entry of moisture until use, the medical material comprising:
      (i) a substrate having first and second opposing sides defining therebetween a predetermined thickness;
      (ii) a reactive system impregnated into or coated onto the substrate, the system remaining stable when maintained in substantially moisture-free conditions and hardening upon exposure to sufficient moisture to form a rigid, self supporting structure; and
      (iii) a soft, flexible, protective, freely water and air permeable padding overlying both the first and second sides of the substrate to provide a cushioning barrier between the substrate and the skin of a patient when the material is in use.

16. A method of constructing a medical bandaging product comprising the steps of:
   (a) providing a moisture-impervious product container comprising an elongate product dispensing sleeve sealable to prevent entry of moisture and a product storage package communicating with the dispensing sleeve;
   (b) providing an elongate medical material positioned in the product storage package of the product container with one end of the material extendable into the dispensing sleeve for being dispensed in an appropriate desired length;
   (c) positioning one end of the medical material in a single layer which coextends with the dispensing sleeve in substantially moisture-free conditions and sealing the medical material in the dispensing sleeve against entry of moisture until use, the medical material comprising:
      (i) a substrate;
      (ii) a reactive system impregnated into or coated onto the substrate, the system remaining stable when maintained in substantially moisture-free conditions and hardening upon exposure to sufficient moisture to form a rigid, self supporting structure; and
      (iii) a soft, flexible protective wrapping enclosing the substrate along its length to provide a cushioning barrier between the substrate and the skin of a patient when the material is in use;
   whereby a desired length of the medical material is removable from the length of bandaging product by dispensing a desired length of bandaging product from within the dispensing sleeve, severing the medical material at a desired point and the end of the dispensing sleeve is sealed against entry of moisture after a desired length of the medical material has been dispensed for use to prevent hardening of the substrate remaining in the dispensing sleeve and in the product storage package.

17. A method of constructing a medical bandaging product according to claim 16, wherein the dispensing sleeve and the storage package each comprise a aluminum foil laminate having an outer tear resistant layer, a central aluminum foil layer and an inner heat sealable plastic layer.

18. A method of constructing a medical bandaging product according to claim 16, wherein the substrate comprises a plurality of knitted or woven fabric layers.

19. A method of constructing a medical bandaging product according to claim 16, wherein the protective wrapping enclosing the substrate comprises a fibrous nonwoven cushion.

20. A method of constructing a medical bandaging product according to claim 16, wherein the protective wrapping enclosing the substrate comprises a nonwoven polypropylene tube.

21. A method of constructing a medical bandaging product according to claim 16, wherein the reactive system comprises a blended polyisocyanate, polyol, catalyst and stabilizer.

22. A method of constructing a medical bandaging product according to claim 16, and including the step of resealing the dispensing sleeve after use of a length of the medical material by using a moisture-impervious tape to seal the open end of the dispensing sleeve.

23. A method of constructing a medical bandaging product according to claim 16, and including the step of resealing the dispensing sleeve after use of a length of the medical material comprises providing at least one resealable interlocking zipper on the end of the dispensing sleeve.

24. A method of constructing a medical bandaging product according to claim 23, wherein two spaced-apart zippers are provided on the end of the dispensing sleeve.

25. A method of constructing a medical bandaging product according to claim 16, and including the step of rolling the bandaging product into a coil and placing the coil in the product storage package with an end of the bandaging product positioned in the dispensing sleeve in preparation for dispensing.

26. A method of constructing a medical bandaging product according to claim 16, and including the step of resealing the dispensing sleeve after use of a length of the medical material comprises clamping the end of the dispensing sleeve with a clamp.

* * * * *

REEXAMINATION CERTIFICATE (3820th)

United States Patent [19]
Parker et al.

[11] B1 5,003,970
[45] Certificate Issued Jul. 27, 1999

[54] ROLL FORM MEDICAL BANDAGING PRODUCT, METHOD OF CONSTRUCTING SAME AND CONTAINER FOR ROLL FORM BANDAGING PRODUCT

[75] Inventors: A. Bruce Parker, Charlotte; Donna F. Miller, Harrisburg, both of N.C.

[73] Assignee: Smith & Nephew Casting, Inc., Memphis, Tenn.

Reexamination Request:
No. 90/004,874, Dec. 18, 1997

Reexamination Certificate for:
Patent No.: 5,003,970
Issued: Apr. 2, 1991
Appl. No.: 07/477,021
Filed: Feb. 8, 1990

Related U.S. Application Data

[63] Continuation-in-part of application No. 07/243,585, Sep. 12, 1988, Pat. No. 4,889,738, which is a continuation of application No. 07/243,584, Sep. 12, 1998, Pat. No. 4,869,046, which is a division of application No. 07/000,815, Jan. 6, 1987, Pat. No. 4,770,299.

[51] Int. Cl.$^6$ ........................................ A61F 13/04
[52] U.S. Cl. ........................... 602/50; 206/389; 206/409; 206/440; 602/6; 602/8
[58] Field of Search ............................................ 602/6–10

[56] References Cited

U.S. PATENT DOCUMENTS

| | | |
|---|---|---|
| 1,208,701 | 12/1916 | Trenner . |
| 2,684,716 | 7/1954 | Mills et al. . |
| 4,002,264 | 1/1977 | Marchesani . |
| 4,535,912 | 8/1985 | Bonk . |
| 4,770,299 | 9/1988 | Parker . |

FOREIGN PATENT DOCUMENTS

| | | |
|---|---|---|
| 360 020 | 4/1906 | France . |
| 2 609 247 A1 | 7/1988 | France . |
| 3800041 A1 | 7/1988 | Germany . |
| 63-288156 | 11/1988 | Japan . |
| 288880 | 6/1953 | Switzerland . |
| 1 586 719 | 3/1981 | United Kingdom . |
| 2 200 286 | 8/1988 | United Kingdom . |

OTHER PUBLICATIONS

Brochure: The first fiberglass splint roll. ORTHO–GLASS™, ©Parker Medical Associates, 4324 Barringer Drive, Suite 111, Charlotte, N.C. 28217 (1988).

Primary Examiner—R. J. Apley

[57] ABSTRACT

An outer container (31) formed of moisture-impervious material having an elongate product dispensing sleeve (32) having a moisture-proof sealable opening (33) on one end and an enlarged product storage package (34) communicating with the dispensing sleeve (32). A medical material (14) is positioned within sleeve (32) and includes a substrate (16) formed of a suitable number of overlaid layers of a woven or knitted fabric such as fiberglass. Substrate (16) is contained within a tubular wrapping (18) formed of a soft, flexible non-woven fiber such as polypropylene. Substrate (16) is impregnated or coated with a reactive system which remains stable when maintained in substantially moisture-free conditions but which hardens upon exposure to sufficient moisture to form a rigid, self-supporting structure.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

THE PATENT IS HEREBY AMENDED AS INDICATED BELOW.

Claims 1, 11, 13, 14, 15 and 16 are determined to be patentable as amended.

Claims 2-10, 12 and 17-26, dependent on an amended claim, are determined to be patentable.

New claims 27 and 28 are added and determined to be patentable.

1. A medical bandaging product for being dispensed in predetermined lengths suitable for a given medical use, comprising:
   (a) an outer container formed of moisture-impervious material, the container comprising an elongated product dispensing sleeve having a moisture-proof sealable opening on one end and an enlarged product storage package communicating with the dispensing sleeve;
   (b) a medical material positioned in the container in substantially moisture-free conditions and sealed therein against entry of moisture until use, the medical material comprising:
   (i) a substrate;
   (ii) a reactive system impregnated into or coated onto the substrate, the system remaining stable when maintained in substantially moisture-free conditions and hardening upon exposure to sufficient moisture to form a rigid, self supporting structure; and
   (iii) a soft, flexible protective wrapping enclosing the substrate along its length to provide a cushioning barrier between the substrate and the skin of a patient when the material is in use;
   (c) *said product dispensing sleeve surrounding the medical material in order to limit exposure of the medical material to air when a predetermined length of the medical material is being withdrawn from the enlarged proudct dispensing container and dispensed through the opening on the end of the dispensing sleeve;*
   [(c)] (*d*) *a dispenser carton for permitting storage of the product dispensing container in a substantially stationary, crush-resistant condition therein, said dispenser including a slot therein through which the elongate product dispensing sleeve is positioned and extended for maintaining the resealable container opening in spaced-apart relation from the medical bandaging product in the enlarged product storage container;*
   (*e*) *means for resealing the dispensing sleeve against entry of moisture after a predetermined length of the bandaging product has been dispensed for use to prevent hardening of the substrate remaining in the product container.*

11. A medical bandaging product according to claim 1, and including a dispenser carton within which the container [is] of medical material is contained.

13. A medical bandaging product in roll form for being dispensed in predetermined lengths suitable for a given medical use, comprising:
   (a) an outer container formed of moisture-impervious material, the container comprising an elongate product dispensing sleeve having an moisture-proof sealable opening on one end and an enlarged product storage package communicating with the dispensed sleeve;
   (b) a medical material positioned in the container in substantially moisture-free conditions and sealed therein against entry of moisture until use, the medical material comprising:
   (i) a substrate formed of a plurality of knitted or woven fabric layers;
   (ii) a reactive system impregnated into or coated onto the substrate, the system remaining stable when maintained in substantially moisture-free conditions and hardening upon exposure to sufficient moisture to form a rigid, self supporting structure and comprising a blended polyisocyanate, polyol, catalyst and stabilizer; and
   (iii) a soft, flexible protective nonwoven tubular web enclosing the substrate along its length to provide a cushioning barrier between the substrate and the skin of a patient when the material is in use;
   (c) *said product dispensing sleeve fitting snugly around the medical material in order to limit exposure of the medical material to air when a predetermined length of the medical material is being withdrawn from the enlarged product dispensing container and dispensed through the opening on the end of the dispensing sleeve;*
   [(c)] (*d*) *a dispenser carton for permitting storage of the product dispensing container in a substantialy stationary, crush-resistant condition therein, said dispenser including a slot therein through which the elongate product dispensing sleeve is positioned and extended for maintaining the resealable container opeining in spaced-apart relation from the medical bandaging product in the enlarged product storage container;*
   (*e*) means for resealing the dispensing sleeve against entry of moisture after a predetermined length of the bandaging product has been dispensed for use to prevent hardening of the substrate remaining in the dispensing sleeve.

14. A medical bandaging product, comprising:
   (a) an outer container formed of moisture-impervious material, the container comprising an elongate product dispensing sleeve having an moisture-proof sealable opening on one end and [a] *an enlarged* product storage package communication with the dispensing sleeve;
   (b) a medical material positioned in the container in substantially moisture-free conditions and sealed therein against entry of moisture until use, the medical material comprising:
   (i) a substrate having first and second opposing sides defining therebetween a predetermined thickness;
   (ii) a reactive system impregnated into or coated onto the substrate, the system remaining stable when maintained in substantially moisture-free conditions and hardening upon exposure to sufficient moisture to form a rigid, self supporting structure; and (iii) a soft, flexible, protective, freely water and air permeable padding overlying both the first and second sides of the substrate contiguous thereto to provide a cushioning barrier between the substrate and the skin of a patient when the material is in use;

(c) *said product dispensing sleeve fitting snugly around the medical material in order to limit exposure of the medical material to air when a predetermined length of the medical material is being withdrawn from the enlarged product dispensing container and dispensed through the opening on the end of the dispensing sleeve; and*

(d) *a dispenser carton for permitting storage of the product dispensing container in a substantially stationary, crush-resistant condition therein, said dispenser including a slot therein through which the elongate product dispensing sleeve is positioned and extended for maintaining the resealable container opening in spaced-apart relation from the medical bandaging product in the enlarged product storage container.*

15. A medical bandaging product, consisting essentially of:

(a) an outer container formed of moisture-impervious material, the container comprising an elongate dispensing sleeve having an moisture-proof sealable opening on one end and an enlarged product storage package communicating with the dispensing sleeve;

(b) a medical material positioned in the container in substantially moisture-free conditions and sealed therein against entry of moisture until use, the medical material comprising:

(i) a substrate having first and second opposing sides defining therebetween a predetermined thickness;

(ii) a reactive system impregnated into or coated onto the substrate, the system remaining stable when maintained in substantially moisture-free conditions and hardening upon exposure to sufficient moisture to form a rigid, self supporting structure; and (iii) a soft, flexible, protective, freely water and air permeable padding overlying both the first and second sides of the substrate to provide a cushioning barrier between the substrate and the skin of a patient when the material is in use;

(c) *said product dispensing sleeve fitting snugly around the medical material in order to limit exposure of the medical material to air when a predetermined length of the medical material is being withdrawn from the enlarged product dispensing container and dispensed through the opening on the end of the dispensing sleeve; and*

(d) *a dispenser carton for permitting storage of the product dispensing container in a substantially stationary, crush-resistant condition therein, said dispenser including a slot therein which the elongate product dispensing sleeve is positioned and extended for maintaining the resealable container opening in spaced-apart relation from the medical bandaging product in the enlarged product storage container.*

16. A method of constructing a medical bandaging product comprising the steps of:

(a) providing a moisture-impervious product container comprising an elongate product dispensing sleeve sealable to prevent entry of moisture and [a] an enlarged product storage package communicating with the dispensing sleeve;

(b) providing an elongate medical material positioned in the product storage package of the product container with one end of the material extendable into the dispensing sleeve *with the dispensing sleeve surrounding the medical material to limit exposure of the medical material to air* for being dispensed in an appropriate desired length;

(c) positioning one end of the medical material in a single layer which coextends with the dispensing sleeve in substantially moisture-free conditions and sealing the medical material in the dispensing sleeve against entry of moisture until use, the medical material comprising:

(i) a substrate;

(ii) a reactive system impregnated into or coated onto the substrate, the system remaining stable when maintained in substantially moisture-free conditions and hardening upon exposure to sufficient moisture to form a rigid, self supporting structure; and (iii) a soft, flexible protective wrapping enclosing the substrate along its length to provide a cushioning barrier between the substrate and the skin of a patient when the material is in use;

(d) *providing a dispenser carton for permitting the storage of the container of medical material in a substantially stationary, crush-resistant condition therein, said dispenser including a slot therein through which the elongate product dispensing sleeve is positioned and extended for maintaining the resealable container opening in spaced-apart relation from the medical bandaging product in the enlarged product storage package;* whereby a desired length of the medical material is removable from the length of bandaging product by dispensing a desired length of bandaging product from within the dispensing sleeve, severing the medical material at a desired point and the end of the dispensing sleeve is sealed against entry of moisture after a desired length of the medical material has been dispensed for use to prevent hardening of the substrate remaining in the dispensing sleeve and in the product storage package.

27. A medical bandaging product according to claim 1, wherein the product dispensing sleeve is snugly fitted around the medical material in order to further limit exposure of the medical material to air.

28. A method of constructing a medical bandaging product according to claim 16, and including the step of providing an elongate medical material positioned in the proudct storage package of the product container with one end of the material extendable into the dispensing sleeve with the dispensing sleeve snugly fitted around the medical material to limit exposure of the medical material to air.

* * * * *